(12) United States Patent
Kalfon (10) Patent No.: US 11,547,547 B2
(45) Date of Patent: Jan. 10, 2023

(54) IMPLANTABLE ANCHORING DEVICE AND METHODS OF USE

(71) Applicant: Allium Medical Solutions LTD., Caesarea Industrial Park South (IL)

(72) Inventor: Ziv Kalfon, Ein Hod (IL)

(73) Assignee: ALLEVETIX MEDICAL LTD., Caesarea Industrial Park South (IL)

(*) Notice: Subject to any disclaimer, the term of this patent is extended or adjusted under 35 U.S.C. 154(b) by 436 days.

(21) Appl. No.: 16/780,948

(22) Filed: Feb. 4, 2020

(65) Prior Publication Data
US 2020/0170775 A1 Jun. 4, 2020

Related U.S. Application Data

(63) Continuation of application No. 16/223,170, filed on Dec. 18, 2018, now Pat. No. 10,631,971, which is a continuation of application No. 15/954,757, filed on Apr. 17, 2018, now Pat. No. 10,368,976.

(60) Provisional application No. 62/613,065, filed on Jan. 3, 2018.

(51) Int. Cl.
*A61F 2/04* (2013.01)
*A61F 5/00* (2006.01)
*A61L 31/02* (2006.01)
*A61L 31/10* (2006.01)

(52) U.S. Cl.
CPC .............. *A61F 2/04* (2013.01); *A61F 5/0036* (2013.01); *A61F 5/0076* (2013.01); *A61L 31/022* (2013.01); *A61L 31/10* (2013.01); *A61F 2002/045* (2013.01); *A61F 2220/0008* (2013.01); *A61F 2220/0033* (2013.01); *A61F 2230/0065* (2013.01); *A61F 2240/001* (2013.01)

(58) Field of Classification Search
CPC ............ A61F 2002/0045; A61F 5/0036; A61F 5/0073; A61B 2017/00588
See application file for complete search history.

(56) References Cited

U.S. PATENT DOCUMENTS

| | | | |
|---|---|---|---|
| 5,059,193 A * | 10/1991 | Kuslich | A61F 2/4455 606/279 |
| 9,636,245 B2 | 5/2017 | Chamorro, III et al. | |
| 2008/0058840 A1 | 3/2008 | Albrecht et al. | |
| 2008/0109027 A1* | 5/2008 | Chen | A61F 5/0036 606/191 |
| 2009/0076615 A1* | 3/2009 | Duggal | A61B 17/7079 623/17.11 |
| 2012/0095484 A1 | 4/2012 | Dominguez | |
| 2012/0209386 A1* | 8/2012 | Triplett | A61F 2/4465 623/17.16 |
| 2014/0012383 A1 | 1/2014 | Triplett et al. | |

(Continued)

*Primary Examiner* — Megan Y Wolf
(74) *Attorney, Agent, or Firm* — Manelli Selter PLLC; Edward Stemberger (57) ABSTRACT

A method of using an implantable device provides an implantable device including a plurality of links (113, 115, 117, 119), a device closure pin (111), a lock-in unit (103) attached and located between two links, and a quick release unit (105) attached and located between two links. The plurality of links (113, 115, 117, 119), lock-in unit (103) and release unit (105) are constructed in a closed contour. The closed contour of the implantable device, in a rigid state (151), is a figure eight comprised of two arcs (125, 127) and two connected interconnecting sections (131, 133).

10 Claims, 8 Drawing Sheets

(56) References Cited

U.S. PATENT DOCUMENTS

2016/0074174 A1\* 3/2016 Halverson ............ A61F 2/4455
                                                             623/17.11
2017/0027621 A1     2/2017 Shenoy
2019/0008654 A1     1/2019 Thommen et al.

\* cited by examiner

SECTION N-N

IMPLANTABLE ANCHORING DEVICE AND METHODS OF USE

The present application is a continuation of U.S. patent application Ser. No. 16/223,170, filed on Dec. 8, 2018, which is a continuation of U.S. patent application Ser. No. 15/954,757 filed on Apr. 17, 2018, now U.S. Pat. No. 10,368,976, which claims the benefit of U.S. Provisional Patent Application 62/613,065 filed on Jan. 3, 2018, all of which are incorporated herein by reference.

TECHNICAL FIELD

The present disclosure generally relates to a device which is inserted into a body cavity using intraoral procedures and positioned within a body cavity by a deformation of the shape and rigidity of the device.

BACKGROUND OF THE DISCLOSURE

Several medical procedures require placement of a medical device in a lumen of human or animal body and in particular in the stomach. Once inserted, the movement of the inserted medical device has to be constrained and this is achieved by use of anchors. U.S. Pat. No. 9,636,245 describes a gastrointestinal device including a proximal element configured to reside in the stomach and a distal element configured to reside in an intestine, where the proximal element is configured to resist migration over time. US Pat. Application No. 2008/0058840 describes an alternative proximal element for placement within a hollow body organ. The proximal element includes a member having a first shape for delivery to the hollow body and a second shape for implantation therein. The member has sufficient rigidity in its second shape to exert an outward force against an interior of the hollow body so as to bring together two substantially opposing surfaces of the hollow body. The examples of implants described in U.S. Pat. No. 9,636,245 and US 2008/0058840 suffer from migration within a lumen of human body, and do not provide the long term required implantation stability.

SUMMARY

This current disclosure describes an implantable device including a plurality of links and configured to be in either of two modes; a flexible mode in at least one plane of the device or a rigid mode in all other planes of the device. The implantable device includes at least but not limited to: device closure pin; a lock-in unit; a quick release unit; a plurality of links where each link is connected to two other links or to a link on one side and either a lock-in unit or release unit on an opposing side. The implantable device is inserted into a body cavity using intraoral procedures. During insertion, the device closure pin is attached only at one side and in one example to the quick release unit, and the implantable device is in the flexible in one plane mode. The flexibility of the implantable device affords the device the ability to follow the contours of the body orifice and facilitates insertion with minimal patient discomfort. The implantable device is releasable connected to the intraoral insertion equipment at the lock-in unit. After insertion of the implantable device into the body and placement of the device in the target body cavity, the device closure pin is pulled into the lock-in unit and locked into place. The device closure pin is now attached at both sides and the implantable device is transformed into a rigid mode providing anchoring features and preventing mobility of the implantable device in the body cavity. In one example a functional unit providing a body related function is attached to release unit. An example of a functional unit is an intragastric sleeve adapted to reduce the intake of food items in the intestine.

DETAILED DESCRIPTION

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure. This disclosure is drawn, inter alia, to a device which is inserted into a human or animal body using intraoral procedures and positioned within a body cavity by a deformation of the shape and rigidity of the device.

In examples/patents of the implantable devices described above, the proximal element is in contact with the pylorus. The shape of the proximal element is rounded and as a result it exerts an expansion force on the pylorus which extends the pylorus opening over time and dislodges the proximal element. Such implants suffer from migration within a lumen of human or animal body, and do not provide the long term required implantation stability. It is desirable to have a proximal element which does have a rounded shape in contact with the pylorus and provides the long term required implantation stability.

Figure 1A:
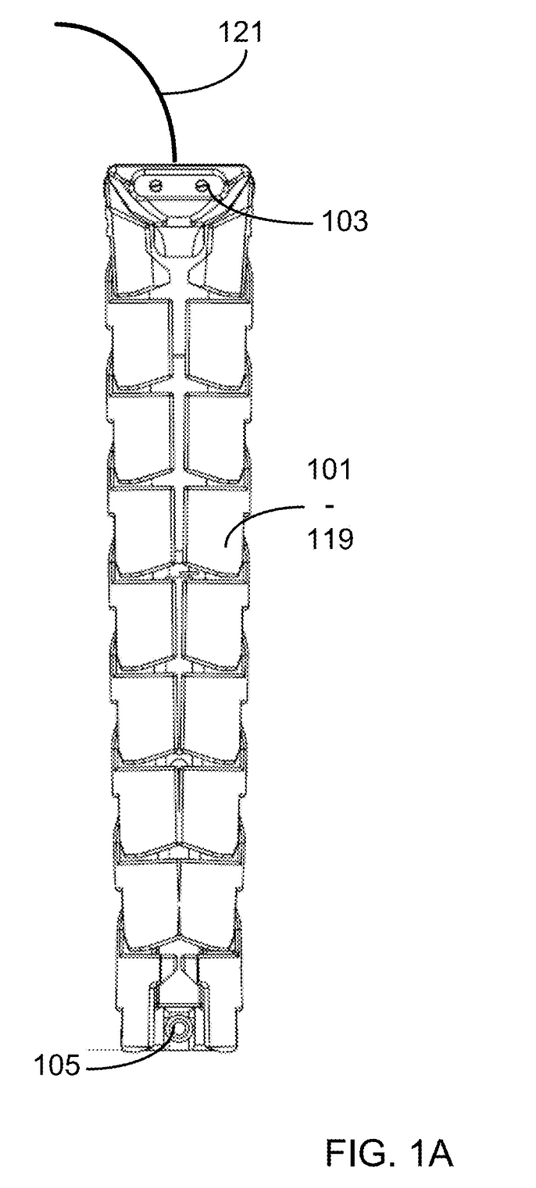
FIG. 1A is an example of an implantable device consisting of a plurality of links and configured to be flexible in at least one plane.

FIG. 1A is an example of an implantable device consisting of a plurality of links and configured to be flexible in at least one plane. The implantable device includes at least but not limited to; a lock-in unit (103); a quick release unit (105); a plurality of links (101, 113, 115, 117, 119) (FIG. 1B) where each link (101, 113, 115, 117, 119) is connected to two other links (101, 113, 115, 117, 119) or to a link (101, 113, 115, 117, 119) on one side and either a lock-in unit (103) or a release unit (105) on an opposing side. The implantable device is inserted into a body cavity using intraoral procedures. During insertion the flexibility of the implantable device affords the device the ability to follow the contours of the body orifice and facilitates insertion with minimal discomfort to the patient. The implantable device is connected to delivery or insertion equipment at lock-in unit (103). In one example a functional unit providing a body related function is attached to release unit (105). An example of a functional unit is an intragastric sleeve adapted to reduce the intake of food items in the intestine.

Figure 1B:
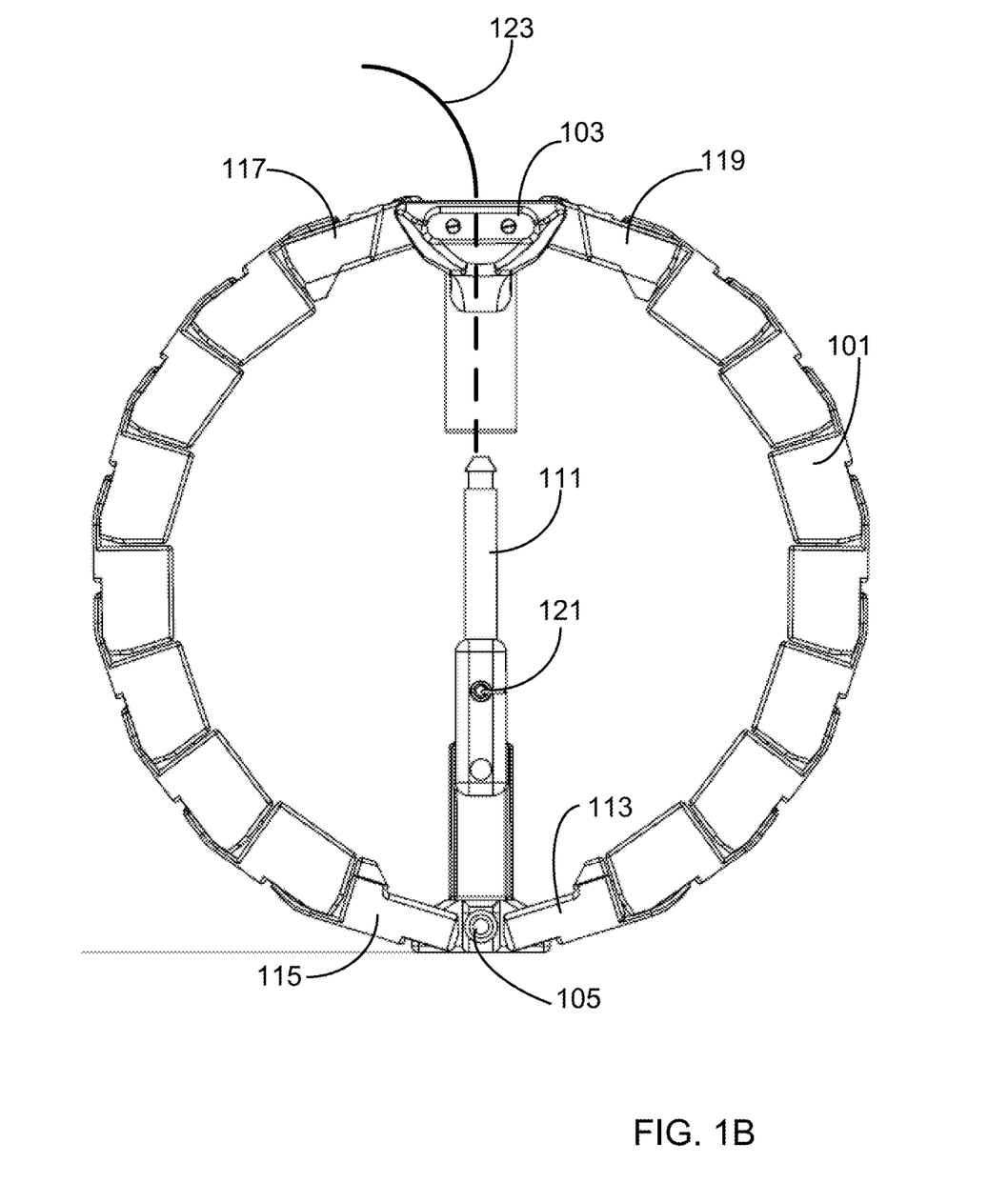
FIG. 1B is an example of an implantable device consisting of multiple links just prior to being configured to be rigid in all planes.

FIG. 1B is an example of an implantable device consisting of multiple links just prior to being configured to be rigid in all planes. The implantable device is transformed from a flexible mode as described in FIG. 1A to a rigid mode as described in FIG. 1C by pulling a chord (123) attached to device closure pin (111) (FIG. 1B) and passing through lock-in unit (103). Device closure pin (111) follows the chord (123) into lock-in unit (103), where a locking mechanism holds the device closure pin (111) in place. The locked in device closure pin (111) exerts a force on the implantable device links (101, 113, 115, 117, 119), constricting the relative movement of the links and transitioning the implantable device to a rigid mode. Transition of the implantable device from a rigid mode to a flexible mode facilitates removal of the implantable device from the body cavity. Removal of release pin (111) from lock-in unit (103), releases the device closure pin from the release unit (105) and transitions the implantable device to a flexible mode. After transitioning the implantable device to a flexible mode, it is removed from the body cavity with intraoral procedures. Examples of materials for manufacturing the links (101, 113, 115, 117, 119) include but are not limited to: Titanium; stainless steel; Cobalt chrome, Nitinol alloy, thermoset plastics and similar materials or composition of said materials. In a further example the links are coated or covered with Teflon or other atraumatic materials. Examples of materials for the device closure pin (111) and the release pin (121) include but are not limited to; stainless steel; titanium; Cobalt chrome, Nitinol alloy, thermoset plastics and similar materials or composition of said materials. In one example the links (101, 113, 115, 117, 119) of the implantable device are manufactured using additive manufacturing processes, for example 3D printing. Links (101, 113, 115, 117, 119), lock in unit (103), quick release unit (105) and interconnecting pins are manufactured concurrently and in a connected manner so that at the additive manufacturing cycle results in a connected closed contour of links (101, 113, 115, 117, 119), lock-in unit (103) and quick release unit (105).

Hence, described in one example is an implantable device including: a plurality of links (101, 113, 115, 117, 119); a device closure pin (111); a lock-in unit (103) attached and located between two links (117, 119); a release unit (105) attached and located between two links (113, 115); wherein the plurality of links (101, 113, 115, 117, 119), lock-in unit (103) and release unit (105) construct a closed contour; and wherein the implantable device is in flexible state when the device closure pin (111) is coupled to the lock-in unit (103) or the release unit (105) and rigid state when the device closure pin (111) is attached to both the lock-in unit (103) and release unit (105).

Figure 1C:
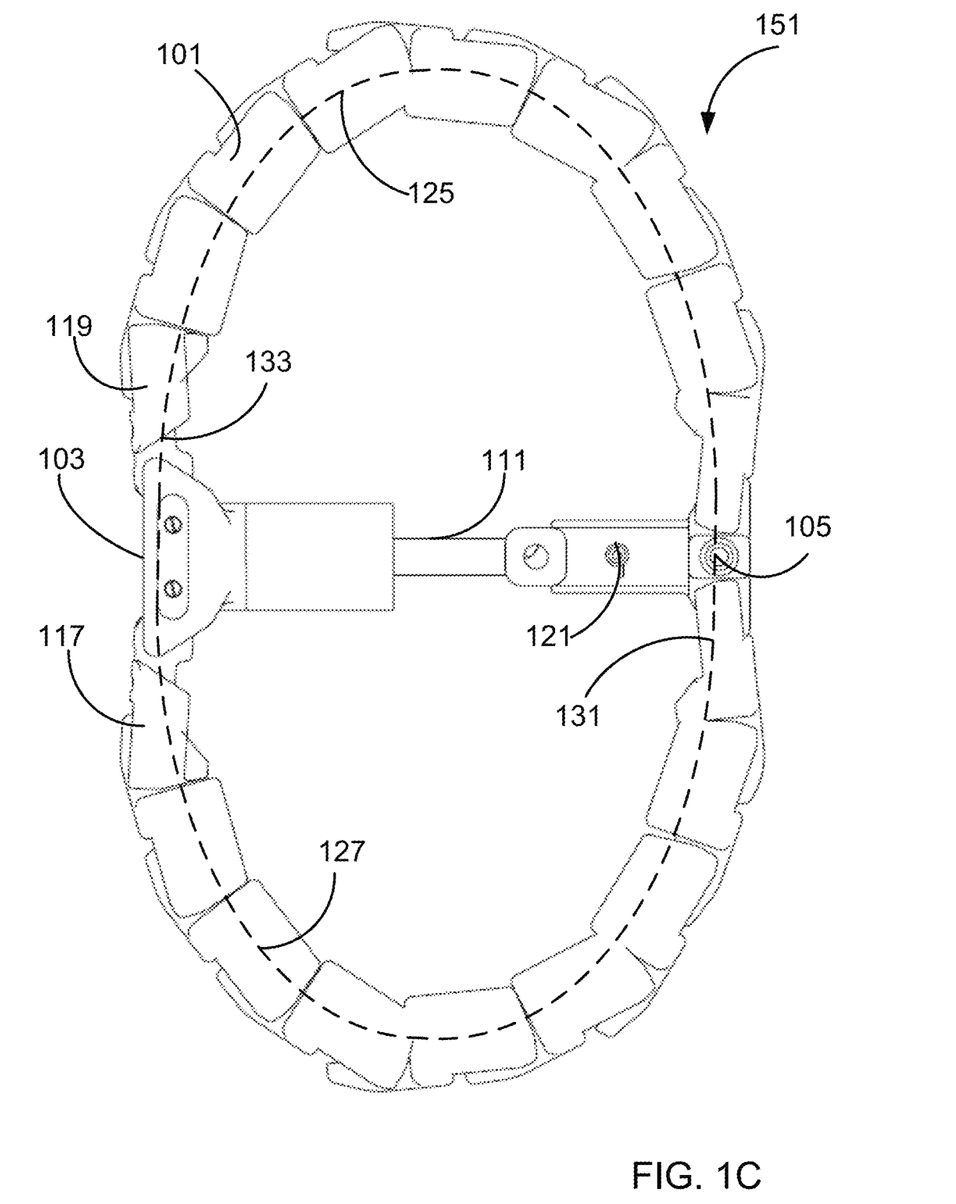
FIG. 1C is an example of an implantable device consisting of multiple links and configured to be rigid in all planes.

FIG. 1C is an example of a side view of the implantable device in the rigid state (151), where the close contour forms and device closure pin (111) form a figure eight. In an alternative example an implantable device comprising; a plurality of links (101, 113, 115, 117, 119) constructing a closed loop wherein a link (101, 111, 113, 115, 117) is connected to two other links (101, 113, 115, 117, 119); a device closure pin (111); wherein the implantable device is flexible when only one side of device closure pin (111) is attached to a link (101, 113, 115, 117, 119) and rigid when both sides of the device closure pin (111) is attached to a link (101, 113, 115, 117, 119). In a further example the closed contour of an implantable device in a rigid state (151) is oval and is configured to follow the shape of two arcs (125, 127) and two interconnecting sections (131, 133) where the absolute radius of the interconnecting sections (131, 133) is at least 5 times the absolute radius of the arcs (125, 127). In a further example the radius of the interconnecting sections (131,133) is opposite the sign of the radius of the arcs (125, 127). In a further example the closed contour of an implantable device in a rigid state is oval and comprised of two arcs (125, 127) and two interconnecting sections (131, 133) where the two interconnecting sections (131, 133) are substantially straight. In a further example the closed contour of an implantable device in a rigid state has a shape of figure eight comprised of two arcs and two connected interconnecting sections. The resulting shape of the implantable device in a rigid state which is in contact with the pylorus is substantially straight and hence does not exert an expanding force on the pylorus, ensuring the long-term stability of the implanted device.

In a further example all link (101, 113, 115, 117, 119) surfaces are atraumatic link surfaces made of titanium. In a further example the atraumatic properties of the links (101, 113, 115, 117, 119) are enhanced by a Teflon coating or overcoat. In a further example the links (101, 113, 115, 117, 119) are fabricated using additive manufacturing processes.

In a further example the release unit (105) includes an extractable pin (121) attaching the device closure pin (111) to the release unit (105) and removal of the extractable pin (121) releases the device closure pin (111) from the release unit (105).

Figure 2A:
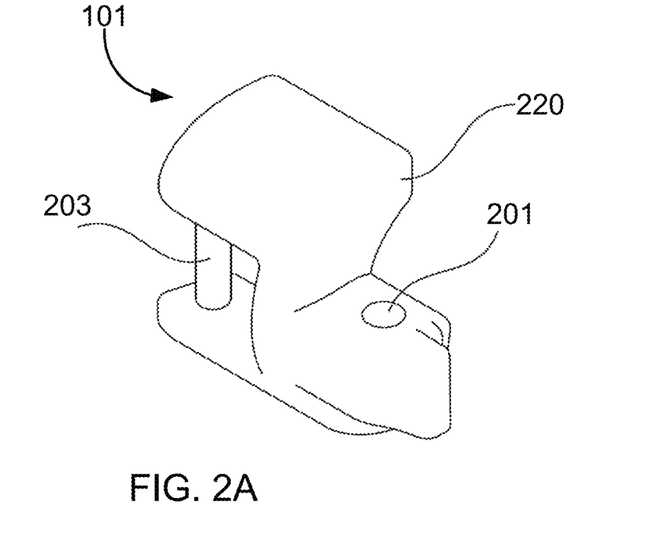
FIG. 2A is an example of a link of the implantable device.
Figure 2B:
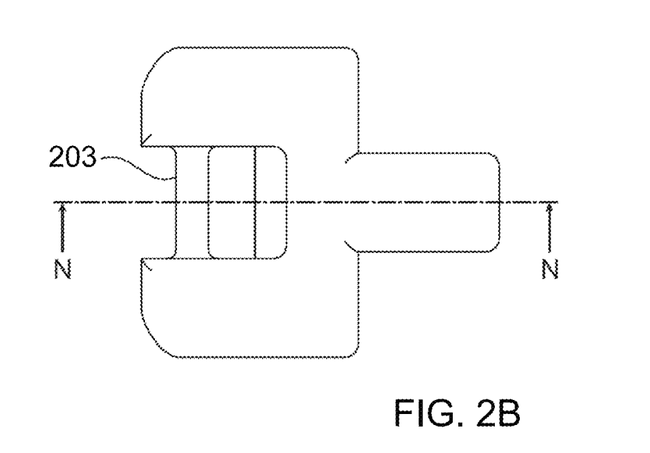
FIG. 2B is an example of a top view of a link of the implantable device.
Figure 2C:
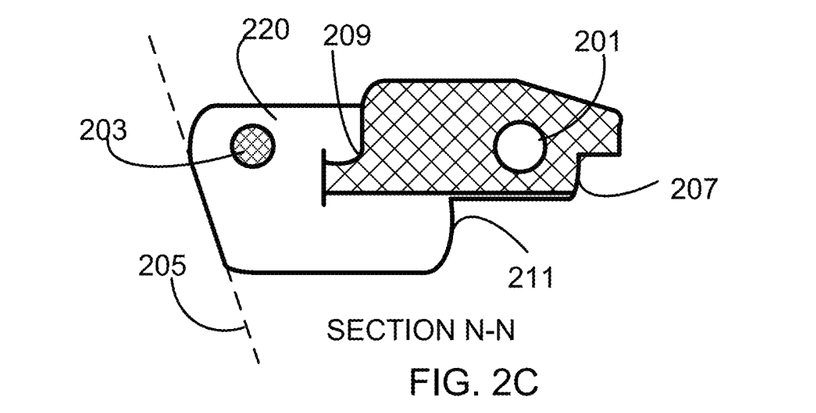
FIG. 2C is an example of a side view cross section of a link of the implantable device at cut line NN from FIG. 2B.

FIG. 2A is an example of an implantable device link (FIG. 1A numerals 101, 113, 115, 117, 119). A link (101) includes an attachment axis (203) and a pin cavity (205). The attachment axis (203) is configured to connect to a pin cavity (201) in a second link so creating a closed contour composed of a plurality of links (101, 113, 115, 117, 119) where each link (101, 113, 115, 117, 119) is connected to two other links (101, 113, 115, 117, 119) or to a link (101) on one side and either a lock in unit (FIG. 1B 103) or release unit (FIG. 1B 105) on an opposing side. FIG. 2B is an example of a top view of a link (101) of the implantable device. FIG. 2C is an example of a side view cross section of a link of the implantable device at cut line N-N from FIG. 2B. The link (101) includes an attachment axis (203) and a pin cavity (201). The link further includes an inclined side (205). In the flexible mode of the implantable device, one link (101) is connected to a second link (101) where the axis (203) of one link (101) is inserted in the pin cavity of a second link (101). The links (101) are free to move around the axle defined by their axis (203). The relative movement of the links (101) around the axle provides the required flexibility along one plane of an implantable device in the flexible mode. In the constrained mode inclined side (205) of one link (101) is pressed against opposing side (211) of adjacent connected link (101). The shape of the contour of the implantable device in the constrained mode is determined by the relative angle of the inclined side (205) of one link (101) and the opposing side (211) of the adjacent link (101) which is in contact with said inclined side (205). In a further example the aforementioned relative angle varies from link to link to configure a specific size shape of the closed contour of the implantable device in the rigid mode.

Support recess (207 or 209) come into contact with support recess (209 or 207) of an adjacent link at a preset maximum angle and provide a constraint on the relative motion of the link (101) in the flexible mode. In a further example the links comprise at least a base (220); one or more connecting pins (203) and one or more vias (201). All links (FIG. 1A 101, 113, 115, 117, 119 and FIG. 2A 101) comprising the implantable device and pins (203) and pin holes (205) are manufactured concurrently so that a pin (203) of one link (101) is situated in a pin hole (205) of an adjacent link (101) or lock in unit (FIG. 1A 103) or quick release unit (FIG. 1A 105) and providing a closed contour of links (101), lock in unit (FIG. 1A 103) and quick release unit (FIG. 1A 105) at the end of the additive manufacturing cycle.

In a further example the links are comprised of at least a base (220); one or more connecting axis (203) and one or more holes (201). In a further example base (220) and a connecting axis (203) of one link (FIG. 1B 101, 111, 113, 115, 117) which is located in a pin hole (201) of a second link (FIG. 1B 101, 111, 113, 115, 117) are fabricated concurrently using additive manufacturing processes.

Figure 3A:
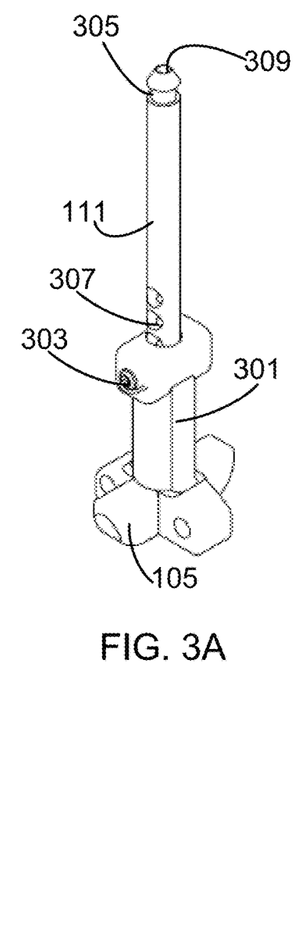
FIG. 3A is an example of device closure pin attached to a release unit.
Figure 3B:
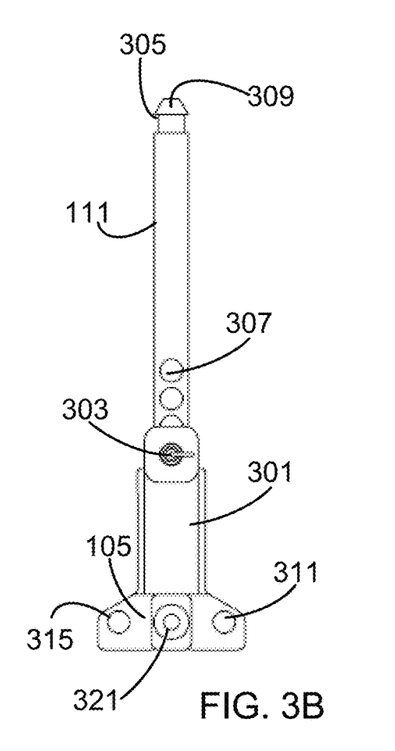
FIG. 3B is an example of a side view of a device closure pin attached to a release unit.
Figure 3C:
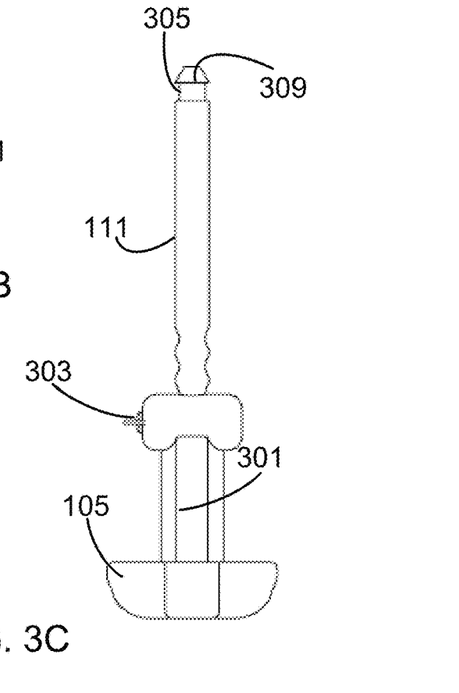
FIG. 3C is an example of a back view of a device closure pin attached to a release unit.

FIG. 3A is an example of a device closure pin (111) attached to a release unit (105). The device closure pin (111) top side is configured as a snap in segment. The snap in segment includes a recess (305) and an angled tip (309). In a further example, when the implantable device is in a flexible mode a chord (FIG. 1B 123) is connected to the top part of the angled tip (309). Pulling the chord (FIG. 1B 123), pulls the device closure pin (111) into a receptacle where it is locked in place due to the recess (305). The device closure pin (111) further includes one or more quick release pin holes (307). FIG. 3B is an example of a side view of a device closure pin attached to a release unit. The device closure unit (105) further includes an attachment pin (315) and attachment pin cavity (311) which correspond to a link's (FIG. 2A 101) attachment pin (FIG. 2C 203) and attachment pin cavity (FIG. 2C 201). The pins are used to attach links on either side of the device closure unit. The device closure unit (105) further includes a quick release housing (301) and second pin hole (303). A device attachment pin is inserted into the quick release housing (301) and held in place by insertion of a quick release pin (FIG. 1B 121) through the second pin hole (303) and quick release pin hole (307) in the device closure pin (111). Prior to insertion in the body the device closure pin (111) is attached to the quick release unit (105). The effective length of the device closure pin (111) is adjusted by a choice through which quick release pin hole (307) the quick release pin (FIG. 1B 121) will pass through and lock the device pin (111) in place. The effective length of the device closure pin (111) determines the contour shape when the implantable device is in the rigid mode. In a further example the contour shape is configured to be essentially flat for at least 1 link on either side of the quick release unit (105). Sleeve connection pin (321) is the anchor point for a chord connecting the implantable device to an intestine sleeve. FIG. 3C is an example of a back view of a device closure pin attached to a release unit.

Figure 4A:
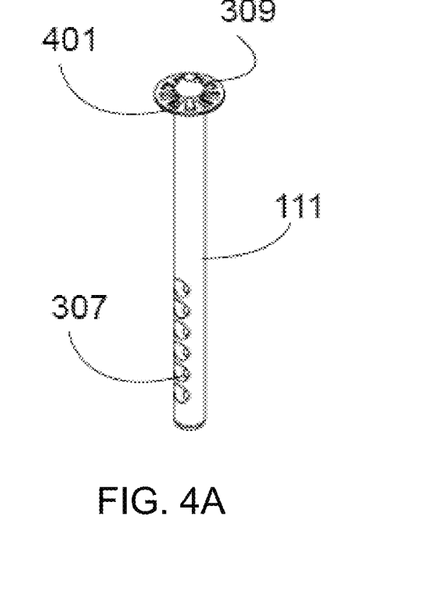
FIG. 4A is an example of device closure pin attached to a receptacle.
Figure 4B:
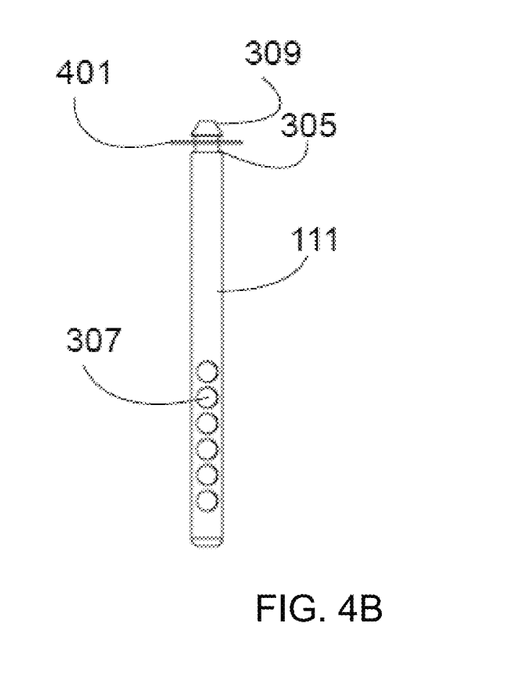
FIG. 4B is an example of a side view of a device closure pin attached to a receptacle.
Figure 4C:
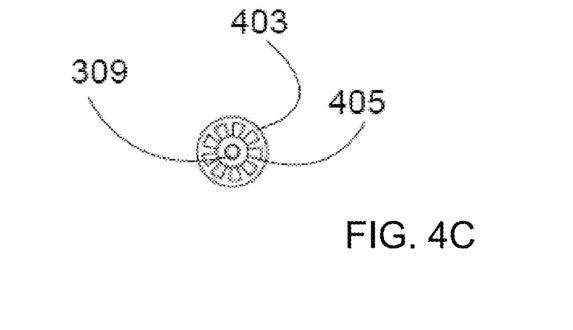
FIG. 4C is an example of a top view of a device closure pin attached to a receptacle.

FIG. 4A is an example of device closure pin (111) attached to a receptacle (401). FIG. 4B is an example of a side view of a device closure pin (111) attached to a receptacle (401) and FIG. 4C is an example of a top view of a device closure pin attached to a receptacle (401). In one example a receptacle (401) includes an outer ring (403) a plurality of spokes (405) which terminate short of the center of the receptacle (401) and enable the angled tip (309) of the device closure pin (111) to traverse the receptacle (401) and then lock the device closure pin (111) in place by extending into the device closure pin recess (305). Examples of materials for manufacturing the receptacle include but are not limited to; stainless steel Titanium; stainless steel; Cobalt chrome, Nitinol alloy, thermoset plastics and similar materials or composition of said materials.

In a further example device closure pin (111) includes an angled tip (309) configured for insertion and lock-in into a receptacle (401) with an outer ring (405) and one or more spokes (403) and in a further example the receptacle (401) is structured as slotted spring washer and configured to receive and hold a snap-in segment of device closure pin (111).

Figure 5:
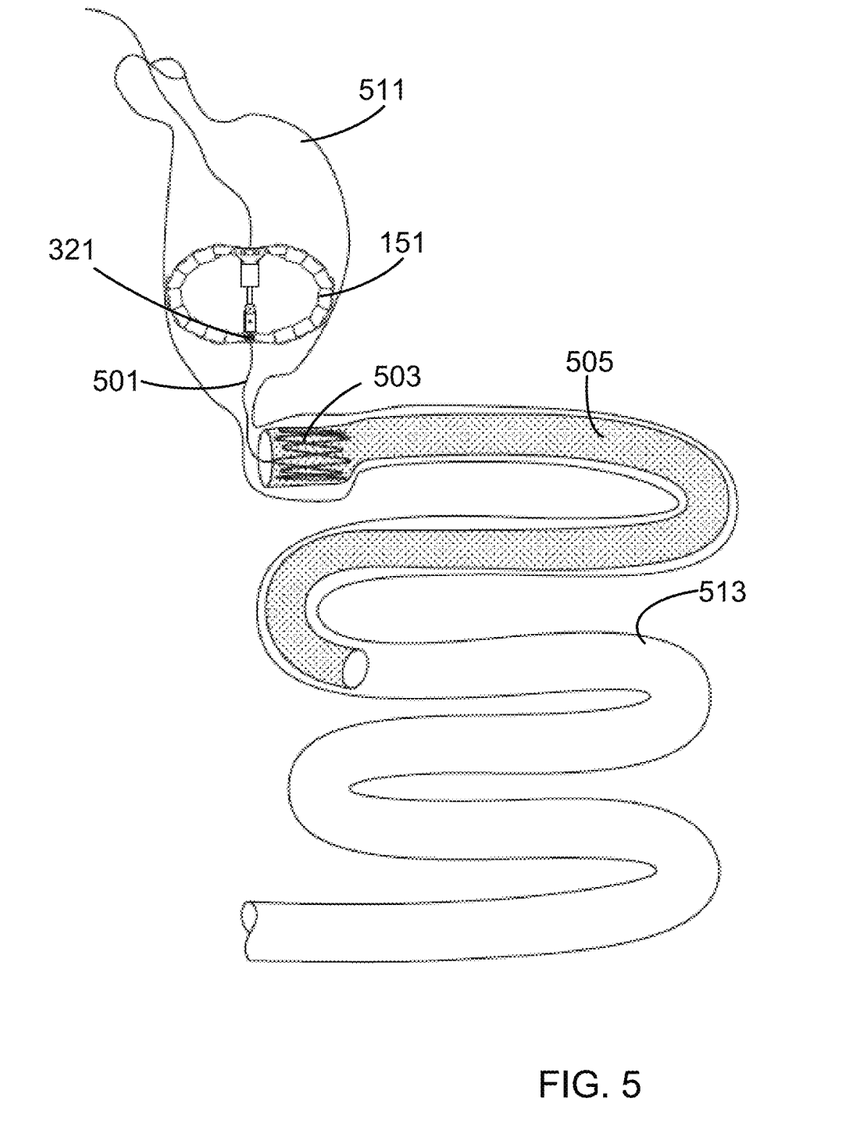
FIG. 5 is an example of a method of use of the implantable device in the rigid state (151) to constrain movement of the device in a body cavity.
Figure 6A:
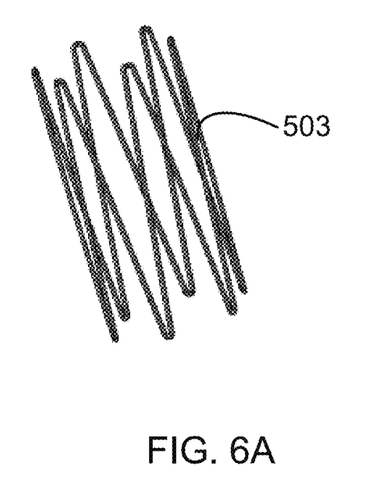
FIG. 6A is an example of the wave anchor (503) in a folded configuration.
Figure 6B:
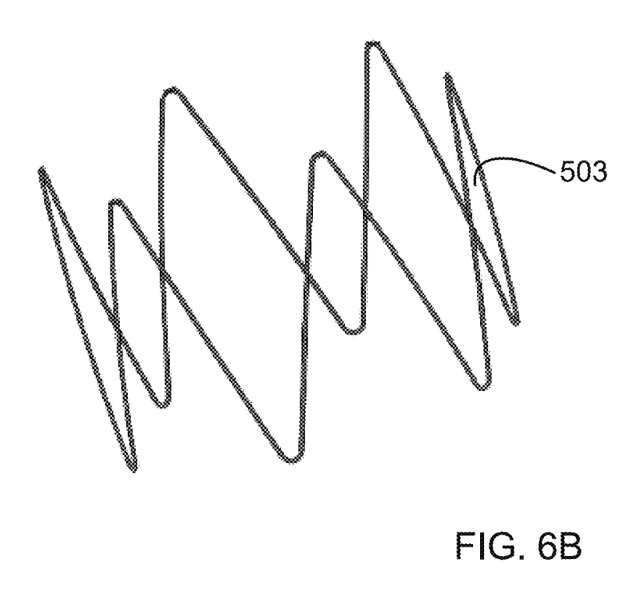
FIG. 6B is an example of the wave anchor in an extended configuration.

FIG. 5 is an example of a method of use of the implantable device in the rigid state (151) to constrain movement in a body cavity. In one example the implantable device in the rigid state (151) is fixed in the stomach (511). An intestine sleeve (505) is attached with the sleeve chord (501) to the implantable device in the rigid state (151) and inserted into the intestine (513). In a further example the intestine sleeve (505) includes a wave anchor (503) which positions it the intestine sleeve in place. FIG. 6A is an example of the wave anchor (503) in a folded configuration and FIG. 6B is an example of the wave anchor in an expanded configuration.

A number of examples have been described. Nevertheless, it will be understood that various modifications may be made without departing from the spirit and scope of the method. Accordingly, other examples are within the scope of the following claims:

What is claimed is:
1. A method of using an implantable device, comprising:
providing an implantable device including a plurality of links (113, 115, 117, 119), a device closure pin (111), a lock-in unit (103) attached and located between two links, and a quick release unit (105) attached and located between two links;
delivering the implantable device in a stomach of a patient; and
constructing the plurality of links (113, 115, 117, 119), lock-in unit (103) and quick release unit (105) in a closed contour,
wherein the closed contour of the implantable device, in a rigid state (151), is a figure eight structure comprised of two arcs (125, 127) and two connected interconnecting sections (131, 133) connected respectively to the quick release unit (105) and lock-in unit (103), with the two connected interconnecting sections extending in a first, generally straight direction and connecting the two arcs and wherein the device closure pin (111) is disposed generally centrally between the two arcs and extends in a second direction generally transverse to the first generally straight direction.

2. The method of claim 1 further comprising attaching the device closure pin (111) to both the lock-in unit (103) and quick release unit (105) and holding the implantable device in a rigid state.

3. The method of claim 1 wherein the plurality of links includes all link surfaces being atraumatic surfaces comprised of titanium.

4. The method of claim 3 wherein the atraumatic surfaces of the links further include a polytetrafluoroethylene coating or overcoat.

5. The method of claim 1 further comprising inserting the device closure pin (111) into a receptacle (401) having an outer ring (403) and one or more spokes (405) which terminate short of the center of the receptacle (401) and enable an angled tip (309) of the device closure pin (111) to traverse the receptacle (401).

6. The method of claim 1 wherein the implantable device is in a flexible state when the device closure pin (111) is coupled to the lock-in unit (103) or the quick release unit (105) and in a rigid state when the device closure pin (111) is attached to both the lock-in unit (103) and the quick release unit (105).

7. The method of claim 1 wherein the quick release unit (105) has an extractable pin (121) attaching the device closure pin (111) to the quick release unit (105) and wherein removing the extractable pin (121) releases the device closure pin (111) from the quick release unit (105).

8. The method of claim 1 wherein the links (113, 115, 117, 119) are fabricated using additive manufacturing processes.

9. The method of claim 1 wherein each of the links (113, 115, 117, 119) includes at least a base (220); an attachment axis (203) and one or more pin holes.

10. The method of claim 9 wherein at least an attachment axis (203) of one link is located in a pin hole of a second link.

\* \* \* \* \*